(12) United States Patent
Kim et al.

(10) Patent No.: US 6,384,245 B1
(45) Date of Patent: May 7, 2002

(54) METHOD FOR PREPARING DL-α-TOCOPHEROL WITH HIGH YIELD

(75) Inventors: Jeong-Soo Kim; Heui-Young Cheong; Sijoon Lee, all of Taejon (KR)

(73) Assignee: SK Corporation, Seoul (KR)

( * ) Notice: Subject to any disclaimer, the term of this patent is extended or adjusted under 35 U.S.C. 154(b) by 2 days.

(21) Appl. No.: 09/697,615

(22) Filed: Oct. 26, 2000

(51) Int. Cl.$^7$ .............................................. C07D 311/72
(52) U.S. Cl. ...................................... 549/408; 549/412
(58) Field of Search ................................. 549/408, 412

(56) References Cited

U.S. PATENT DOCUMENTS

| | | | |
|---|---|---|---|
| 4,217,285 A | 8/1980 | Yoshino et al. | 260/345.5 |
| 4,634,781 A | 1/1987 | Finnan | 549/411 |
| 4,639,533 A | 1/1987 | Finnan | 549/411 |

Primary Examiner—T. A. Solola
(74) Attorney, Agent, or Firm—Abelman, Frayne & Schwab

(57) ABSTRACT

Disclosed is a method for preparing DL-α-tocopherol with a high yield through the condensation of isophytol or phytol derivatives with trimethylhydroquinone (TMHQ) in the presence of a Zn—Al heterogeneous catalyst system. At 80 to 120° C., the condensation is carried out for 2 to 7 hours in the presence of a Zn(II) ion-coated alumina-silica catalyst in an n-heptane solvent. The synthetic Zn(II) ion-coated silica-alumina synthetic catalyst system can remarkably reduce side-reactions upon the condensation of isophytol or phytol derivatives and TMHQ, thus producing DL-α-tocopherol with a high purity at a high yield. In addition, the catalyst system is greatly convenient to handle and therefore apply for continuous reactions for the preparation of DL-α-tocopherol. With these advantages, the catalyst system can be effectively used in preparing highly pure DL-α-tocopherol at a high yield on a commercial scale.

7 Claims, No Drawings

METHOD FOR PREPARING DL-α-TOCOPHEROL WITH HIGH YIELD

BACKGROUND OF THE INVENTION

1. Field of the Invention

The present invention relates to a preparation method of DL-alpha-tocopherol through the condensation between isophytol or phytol derivatives and trimethylhydroquinone (TMHQ) in the presence of a Zn—Al heterogeneous catalyst. More particularly, the present invention relates to a Zn(II)-coated silica-alumina synthetic catalyst which is anchored with a Zn and an Al site, simultaneously and thus are very effective in the preparation of DL-α-tocopherol with high yield.

2. Description of the Prior Art

For the past few decades, extensive effort has been made to effectively prepare DL-α-tocopherol by use of Zn(II) ions as metallic catalysts (Lewis acid catalyst). Conventionally, the DL-α-tocopherol is prepared through the condensation of an isophytol and trimethylhydroquinone (TMHQ) represented by the following reaction formula 1:

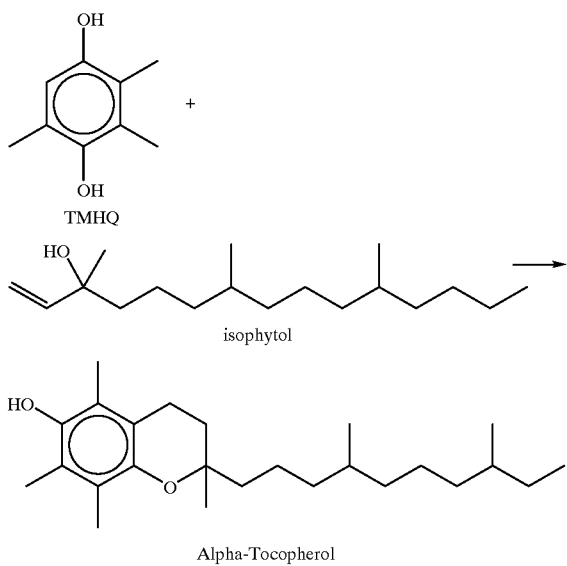

For example, U.S. Pat. No. 4,217,285 (hereinafter '285 patent) discloses the synthesis of DL-α-tocopherol in toluene or n-hexane solvent with $ZnCl_2$ and silica-alumina (or silica-gel) in the presence of acid, especially HCl, asserting that tocopherol can be obtained with a purity of 95 to 96% at a production yield of 99% or higher. Also, U.S. Pat. Nos. 4,634,781 and 4,639,533, both assigned to BASF, disclose processes producing for DL-α-tocopherol in which isophytol is reacted with amines such as a tridecylamine and thereafter with TMHQ in the presence of $ZnCl_2$ and HCl, which are somewhat complicated and inefficient. In those cases, the tocopherol is described to be produced with a purity of 94 to 95% at a yield of 95 to 98%.

However, the conventional techniques leave room for improving purity because their DL-α-tocopherol is as low as 95% pure on average. Particularly, the BASF patents are inefficient in that they do not satisfy the desired yield of DL-α-tocopherol.

Being used as a solvent in the '285 patent, toluene or hexane brings about a poor result in the total yield of DL-α-tocopherol. When used, toluene itself is partially reacted with isophytol to be produced undesired by-products. Hexane, although not reacting with isophytol, lengthens the reaction time owing to its low boiling point (approximately 69° C.) such that the catalyst aggravates the dehydration of isophytol. Furthermore, when the synthesis of DL-α-tocopherol is carried out in such a reaction procedure, by-products analogous in structure to DL-α-tocopherol are found in relatively large quantities, decreasing the purity of the DL-α-tocopherol. This is made worse when acid or base is used as a co-catalyst. In the case of $ZnCl_2$ alone, not together with an Al-based catalyst such as $AlCl_3$ or $SiO_2$—$Al_2O_3$, analogous by-products appear in abundance. Moreover, the conventional techniques suffer from the serious problem of having to treat the waste water resulting from the use of acid or base such as hydrochloric acid.

SUMMARY OF THE INVENTION

Knowledge of catalytic reaction mechanisms allows modification and adaptation leading to the present invention.

The intensive and extensive research on the preparation of DL-α-tocopherol, conducted by the present inventors, resulted in the finding that a novel catalyst system obtained by coating $ZnCl_2$ on silica-alumina through sintering is useful for us to prepare highly pure DL-α-tocopherol at a high yield with ease.

The effectiveness of $ZnCl_2$ and silica-alumina was supported by various experiments with $ZnCl_2$ and $AlCl_3$-mixed catalyst systems, which led to the result that the Zn(II) ion plays an important role in the synthesis of DL-α-tocopherol as a catalyst while, acting as an ancillary catalyst, the Al(III) ion reduces side-reactions and increases the purity of the final product. On the whole, a Zn—Al mixed catalyst system was found to enable a pure DL-α-tocopherol to be synthesized at a high yield.

Based on this finding, the present inventors developed a Zn(II) ion catalyst system into a Zn—Al based catalyst system which affords an ideal synthetic site for DL-α-tocopherol. After extensive trials, a silica-alumina catalyst coated with Zn(II) ions was found to be the most effective in preparing DL-α-tocopherol from a minimum amount of isophytol or phytol derivatives while generating substantially no by-products.

Therefore, it is an object of the present invention to provide a method for preparing DL-α-tocopherol at a high yield with greater ease.

It is another object of the present invention to provide a method for preparing DL-α-tocopherol, which can be applied for continuous reactions for the production of DL-α-tocopherol on a commercial scale with a great convenience.

It is a further object of the present invention to provide a method for preparing DL-α-tocopherol, which generates substantially no by-products, so as to use expensive isophytol or phytol derivatives at a minimum amount.

Based on the present invention, the above objects could be accomplished by providing a method for preparing DL-α-tocopherol at a high yield, comprising condensation reacting isophytol or phytol derivatives with trimethylhydroquinone at 80 to 120° C. for 2 to 7 hours in the presence of a Zn(II) ion-coated silica-alumina catalyst system in hydrocarbon solvent, particularly in n-heptane solvent.

DETAILED DESCRIPTION OF THE INVENTION

In accordance with the present invention, DL-α-tocopherol is prepared through the condensation between isophytol or phytol derivatives and TMHQ in the presence of a Zn(II) ion-coated silica-alumina heterogeneous catalyst in a non-polar solvent.

Available in the present invention is isophytol or phytol derivatives represented by the following chemical formula I or II:

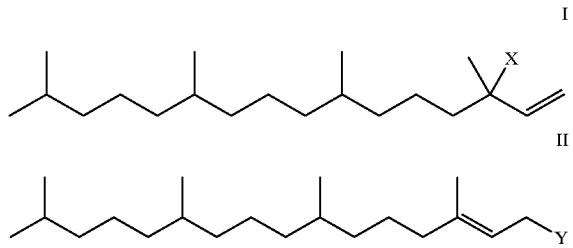

wherein X and Y are independently a hydroxy group, a halogen atom or an acetoxy group.

Fundamentally, mixed catalyst systems in the prior art suffer from the problem caused by employing component catalysts separately. In addition, they are not convenient to handle. With these disadvantages, conventional mixed catalyst systems are considerably difficult to apply for continuous processes for the preparation of DL-α-tocopherol. However, the problems with the conventional catalyst systems can be overcome by the catalyst system according to the present invention, which has Zn(II) coated on silica-alumina. The suitable catalyst in the present invention is made in the form of a Zn(II) supported silica-alumina, such that is anchored with a Zn(II) and an Al(III) site, simultaneously. The coating of Zn(II) ions on the silica-alumina support is achieved by impregnating $ZnCl_2$ into a silica-alumina support and sintering the $ZnCl_2$ impregnated support at about 400° C. for 2 hours. For instance, a catalyst system obtained after $ZnCl_2$ was used at an amount of 50% by weight of silica-alumina upon the sintering, was analyzed for the composition thereof and the result is given in Table 1, below, demonstrating that $ZnCl_2$ is found to be successfully impregnated into the silica-alumina support.

TABLE 1

| Component | Si | Al | Zn | Cl |
|---|---|---|---|---|
| Wt. (%) | 21.6 | 12.6 | 17.9 | 12.7 |

When DL-α-tocopherol was prepared in the presence of this catalyst, the resulting product was found to be as good as or better than that when in the presence of $ZnCl_2$ and silica-alumina, separately. This finding proves beyond doubt the ability of the catalyst according to the present invention to provide an ideal environment for the preparation of DL-α-tocopherol.

A preferable result is obtained when the catalyst of the present invention is used at an amount of 20 to 450 weight parts based on 100 weight parts of TMHQ. The range of 100 to 200 weight parts of the catalyst brings about a more preferable result in the preparation of DL-α-tocopherol. In preparing the catalyst according to the present invention, $ZnCl_2$ is preferably used at an amount of 5 to 250 weight parts based on 100 weight parts of silica-alumina and most preferably at an amount of 20 to 80 weight parts. With respect to the catalytically effective quantity, an excellent product of tocopherol is obtained when the amount of the catalyst is maintained in a specific range to the amount of TMHQ as well as when the amount ratio of $ZnCl_2$ to $SiO_2$—$Al_2O_3$ is maintained within such a range.

Examples of the solvent useful in the present invention include aromatic solvents such as toluene, benzene and xylene and aliphatic saturated hydrocarbon solvents such as n-heptane, n-hexane and n-octane with a preference for toluene and n-heptane. Of them, n-heptane guarantees the most preferable synthesis results in the present invention.

The most preferable period of reaction time falls within the range of 2 to 7 hours, while suitable reaction temperatures are in the range of 80 to 120° C.

In the following Table 2, there are given reaction conditions and their results.

TABLE 2

Preparation of DL-α-Tocopherol According to Reaction Conditions

| Catalyst | Solvent | Rxn Temp. (° C.) | Rxn Time (hr) | Yield (%) | Purity (%) |
|---|---|---|---|---|---|
| $ZnCl_2$/Si-Al | Toluene | 110 | 3 | 93.6 | 99.4 |
| $ZnCl_2$-coated Si-Al | n-Heptane | 99 | 4 | 99.4 | 99.1 |
| $ZnCl_2$-coated Si-Al | Toluene | 110 | 3 | 93.3 | 99.1 |

Analysis of all the reaction products was conducted by use of gas phase chromatography (HP-5890 series) with HP-1 columns.

Summarized in Table 2 are the results obtained by the reaction equivalents of TMHQ and isophytol with each other in the two solvents in accordance with catalysts. As apparent in Table 2, the product obtained using the Zn(II)-coated Si—Al catalyst is almost equal to that obtained through use of a catalyst mixture of $ZnCl_2$ and Si—Al in the same solvent. When toluene was used, approximately 6% of TMHQ remained unreacted as seen from the production yield of 93 to 94%. Thus, the corresponding amount of isophytol did not take part in the reaction and was found to be decomposed by the catalyst. On the other hand, n-heptane improved the production yield to at least 99%, leaving TMHQ unreacted at a level of 1% or less. Thus, 99% or more of the isophytol took part in the reaction while the corresponding amount, that is, 1% or less of isophytol was decomposed by the catalyst. This result indicates that isophytol is more stable in heptane than in other solvents. Consequently, the employment of heptane as a reaction solvent can minimize the amount of isophytol needed to completely react a given amount of TMHQ, thereby reducing raw material cost for the production of DL-α-tocopherol.

A better understanding of the present invention may be obtained in light of the following examples which are set forth to illustrate, but are not to be interpreted to limit the present invention.

COMPARATIVE EXAMPLE 1

A 100 ml round-bottom flask equipped with a Dean-Stark device and a condenser was purged with nitrogen, after which 3 g of TMHQ and 1 g of $ZnCl_2$ were placed in the flask and added with 50 ml of toluene and the solution was stirred. After 2 g of silica-alumina was added into the solution, the flask was equipped with a dropping funnel with nitrogen purging through the flask. A solution of 6 g of isophytol in 10 ml of toluene was placed in the dropping funnel and the flask was heated for refluxing under the nitrogen atmosphere. On refluxing, the solution of isophytol in toluene was slowly added into the flask over 2 hours. After completion of the addition, reflux was carried out for another hour. The product mixture was analyzed by GC, and the conversion of TMHQ was found to be 93% and the purity of DL-α-tocopherol to be 99% or higher.

PREPARATION EXAMPLE

Preparation of Zn(II) Ion-Coated Silica-Alumina Catalyst

In a mixture of 15 g of $H_2O$ and 3 g of a 35% HCl aqueous solution was dissolved 15 g of $ZnCl_2$ and then, added 30 g of silica-alumina. For impregnating $ZnCl_2$ onto the silica-alumina, the precipitate was filtered followed by drying and sintering at 400° C. for 2 hours to provide a Zn(II) ion-coated silica-alumina catalyst.

EXAMPLE 1

Under the same reaction condition as in Comparative Example 1, 3 g of TMHQ and 4 g of the catalyst prepared in accordance with PREPARATION EXAMPLE were placed in the flask and 50 ml of n-heptane is added as a solvent. On refluxing, a solution of 6 g of isophytol in n-heptane is slowly added under the nitrogen atmosphere. After completion of the addition, reflux was kept out for 2 more hours. The product mixture was analyzed by GC, and the conversion of TMHQ was found to be 99% or higher and the purity of DL-α-tocopherol to be 99% or higher.

As described hereinbefore, the Zn(II) ion-coated silica-alumina catalyst system according to the present invention can remarkably reduce side-reactions upon the condensation between isophytol and TMHQ in comparison with the conventional catalysts for use in preparing DL-α-tocopherol; thus, producing DL-α-tocopherol with a high purity at a high yield. In addition, the catalyst system according to the present invention is greatly improved in being handled and applied for continuous reactions for the preparation of DL-α-tocopherol. With these advantages, the Zn(II) ion-coated silica-alumina catalyst according to the present invention can be effectively used in preparing highly pure DL-α-tocopherol at a high yield on a commercial scale.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing DL-α-tocopherol at a high yield, comprising condensation reacting isophytol or phytol derivatives with trimethylhydroquinone at 80 to 120° C. for 2 to 7 hours in the presence of a Zn(II) ion-coated silica-alumina catalyst in an n-heptane solvent.

2. The method as set forth in claim 1, wherein the Zn(II) ion-coated silica-alumina catalyst is prepared by impregnating $ZnCl_2$ into a silica-alumina supporter and sintering the $ZnCl_2$ impregnated supporter at 400° C. for 2 hours.

3. The method as set forth in claim 2, wherein $ZnCl_2$ is used at an amount of 5 to 250 weight parts based on 100 weight parts of the silica-alumina supporter.

4. The method as set forth in claim 2, wherein $ZnCl_2$ is used at an amount of 20 to 80 weight parts based on 100 weight parts of the silica-alumina supporter.

5. The method as set forth in claim 1, wherein the isophytol or phytol derivatives are represented by the following chemical formula I or II:

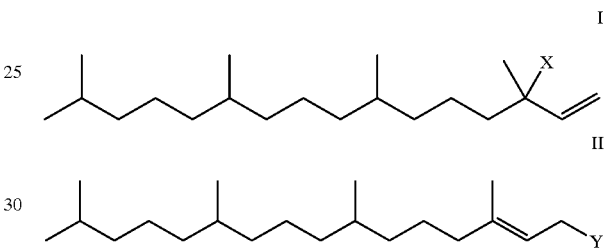

wherein, X and Y are independently a hydroxy group, a halogen atom or an acetoxy group.

6. The method as set forth in claim 1, wherein the catalyst is used at an amount of 20 to 450 weight parts based on 100 weight parts of trimethylhydroquinone.

7. The method as set forth in claim 1, wherein the catalyst is used at an amount of 100 to 200 weight parts based on 100 weight parts of trimethylhydroquinone.

\* \* \* \* \*